(12) United States Patent
Serra

(10) Patent No.: US 8,642,565 B2
(45) Date of Patent: Feb. 4, 2014

(54) INCREASE OF IMMUNE RESPONSE AND TARGETING BY ANTIGENS AND/OR DRUG LINKAGE

(75) Inventor: Vincent Serra, Bondoufle (FR)

(73) Assignee: Wittycell, Reims (FR)

( * ) Notice: Subject to any disclaimer, the term of this patent is extended or adjusted under 35 U.S.C. 154(b) by 509 days.

(21) Appl. No.: 12/741,980

(22) PCT Filed: Nov. 7, 2008

(86) PCT No.: PCT/EP2008/065179
§ 371 (c)(1),
(2), (4) Date: Aug. 20, 2010

(87) PCT Pub. No.: WO2009/060086
PCT Pub. Date: May 14, 2009

(65) Prior Publication Data
US 2010/0330111 A1  Dec. 30, 2010

Related U.S. Application Data

(60) Provisional application No. 60/996,226, filed on Nov. 7, 2007.

(30) Foreign Application Priority Data

Nov. 7, 2007 (EP) ................................. 07291336

(51) Int. Cl.
*A61K 39/00* (2006.01)
*A61K 38/17* (2006.01)
*C07H 15/04* (2006.01)

(52) U.S. Cl.
USPC ........................ 514/25; 536/17.9; 424/184.1

(58) Field of Classification Search
None
See application file for complete search history.

(56) References Cited

U.S. PATENT DOCUMENTS

| | | | |
|---|---|---|---|
| 4,294,854 A | 10/1981 | Durant et al. | |
| 5,242,800 A | 9/1993 | Jimenez et al. | |
| 5,604,207 A | 2/1997 | DeFrees et al. | |
| 5,767,092 A | 6/1998 | Koezuka et al. | |
| 5,780,441 A | 7/1998 | Higa et al. | |
| 5,785,975 A | 7/1998 | Parikh | |
| 5,849,716 A | 12/1998 | Akimoto et al. | |
| 5,936,076 A | 8/1999 | Higa et al. | |
| 5,958,426 A | 9/1999 | Moreau et al. | |
| 6,054,433 A | 4/2000 | Elias et al. | |
| 6,071,884 A | 6/2000 | Koezuka et al. | |
| 6,417,167 B1 | 7/2002 | Maruyama et al. | |
| 6,531,453 B1 | 3/2003 | Taniguchi et al. | |
| 6,610,835 B1 | 8/2003 | Liotta et al. | |
| 6,635,622 B2 | 10/2003 | Tomiyama et al. | |
| 6,747,010 B2 | 6/2004 | Taniguchi et al. | |
| 7,273,852 B2 | 9/2007 | Tsuji et al. | |
| 7,273,853 B2 | 9/2007 | Or et al. | |
| 7,645,873 B2 | 1/2010 | Savage et al. | |
| 7,989,423 B2 | 8/2011 | Savage et al. | |
| 8,207,135 B2 * | 6/2012 | Serra ............................. 514/25 | |
| 8,211,861 B2 * | 7/2012 | Serra ............................. 514/25 | |
| 2002/0115624 A1 | 8/2002 | Behar et al. | |
| 2003/0139351 A1 | 7/2003 | Taniguchi et al. | |
| 2003/0153514 A1 | 8/2003 | Yagita | |
| 2003/0157113 A1 | 8/2003 | Terman | |
| 2003/0157135 A1 | 8/2003 | Tsuji et al. | |
| 2004/0127429 A1 | 7/2004 | Tsuji | |
| 2004/0166554 A1 | 8/2004 | Chamoles | |
| 2004/0266726 A1 | 12/2004 | Yagita | |
| 2005/0192248 A1 | 9/2005 | Tsuji et al. | |
| 2005/0222048 A1 | 10/2005 | Tsuji et al. | |
| 2006/0019246 A1 | 1/2006 | Tsuji et al. | |
| 2006/0073118 A1 | 4/2006 | Bendelac et al. | |
| 2006/0211856 A1 | 9/2006 | Tsuji et al. | |
| 2008/0095787 A1 | 4/2008 | Teyton | |
| 2008/0279894 A1 | 11/2008 | Teyton et al. | |
| 2009/0047299 A1 * | 2/2009 | Savage et al. .............. 424/184.1 | |

FOREIGN PATENT DOCUMENTS

| | | |
|---|---|---|
| EP | 0988860 | 3/2000 |
| EP | 1016409 | 7/2000 |
| WO | WO 99/33475 | 7/1999 |
| WO | WO 03/009812 | 2/2003 |
| WO | WO 03/018039 | 3/2003 |
| WO | WO 03/105769 | 12/2003 |
| WO | WO 2004/094444 | 11/2004 |
| WO | WO 2005/000348 | 1/2005 |
| WO | WO 2005/102049 | 11/2005 |
| WO | WO 2006/026389 | 3/2006 |
| WO | WO 2006/029010 | 3/2006 |
| WO | WO 2006/083671 | 8/2006 |
| WO | WO 2007/007946 | 1/2007 |
| WO | WO 2007/050668 | 5/2007 |
| WO | WO 2007/051004 | 5/2007 |
| WO | WO 2008/005824 | 1/2008 |
| WO | WO 2008/080926 | 7/2008 |

OTHER PUBLICATIONS

Zhou et al., Organic Letters, vol. 4, No. 8, 2002, pp. 1267-1270.*

(Continued)

*Primary Examiner* — Traviss C McIntosh, III
(74) *Attorney, Agent, or Firm* — Merchant & Gould P.C.

(57) ABSTRACT

The present invention relates to compounds consisting of glycolipids covalently bound to an antigen or a drug via a linker. The said compounds are able to induce a stronger immune response than a composition comprising separated glycolipids and antigen. The said compounds are also able to target drug to CD1d restricted cells.

15 Claims, 6 Drawing Sheets

(56) References Cited

OTHER PUBLICATIONS

Ando et al., "Solid-phase capture-release strategy applied to oligosaccharide synthesis on a soluble polymer support," *Agnew. Chem. Int. Ed.* (2001) 40:4725-4728.

Beaudoin, L. et al., "NKT cells inhibit the onset of diabetes by impairing the development of pathogenic T cells specific for pancreatic beta cells," *Immunity* (2002) 17:725-736.

Bendelac et al., "Increased interleukin 4 and immunoglobulin E production in transgenic mice overexpressing NK1 T cells," *J. Exp. Med.* (1996) 184: 1285-1293.

Bendelac, A. et al., "Autoreactivity by design: innate B and T lymphocytes," *Natur. Rev. Immunol.* (2001) 1:177-186.

Bendelac, A. et al., "The biology of NKT cells," *Ann. Rev. Immunol.* (2007) 25:297-336.

Bendelac, A., "Nondeletional pathways for the development of autoreactive thymocytes," *Nat. Immunol.* (2004) 5:557-558.

Benlagha, K. et al., "In vivo identification of glycolipid antigen-specific T cells using fluorescent CD1d tetramers," *J. Exp. Med.* (2000) 191:1895-1903.

Brigl et al., "Mechanism of CD1d-restricted natural killer T cell activation during microbial infection," *Nat. Immunol.* (2003) 4: 1230-1237.

Brigl et al., "T cell function and antigen presentation," *Annu. Rev. Immunol.* (2004) 22: 817-890.

Brossay, L. et al., "Cutting edge: structural requirements for galactosylceramide recognition by CD1-restricted NK T cells," *J. Immunol.* (1998) 161(10):5124-5128.

Brutkiewicz et al., "CD1d-mediated antigen presentation to natural killer T (NKT) cells," *Critical Reviews in Immunology* (2003) 23: 403-419.

Brutkiewicz et al., "Natural killer T (NKT) cells and their role in antitumor immunity," *Critical Reviews in Oncology/Hematology* (2002) 41: 287-298.

Cantu et al., "The paradox of immune molecular recognition of alpha-galactosylceramide; low affinity, low specificity for CD1d, high affinity for alpha beta TCRs," *J. Immunol.* (2003) 170: 4673-4682.

Cochlovius et al., "Therapeutic Antibodies", Modern Drug Discovery, 2003, pp. 33-38.

Corey et al., "A new method for the synthesis of organic nitro compounds," *J. Am. Chem. Soc.* (1984) 106:3682-3683.

Daoudi, J-M. et al., "New bicyclam-galcer analogue conjugates: synthesis and in vitro anti-HIV activity," *Biorg. Med. Chem. Lett.* (2004) 14:495-498.

Dascher, C.C. et al., "CD1 Antigen Presentation and Infectious Disease," *Contributions to Microbiology* (2003) 10:164-182.

Davis, N.J. et al., "Chemical Synthesis of Disaccharides Which are Partial Structures of the Glycosaminoglycan Heparan Sulfate," *J. Chem. Soc.* (1994) 1:359-368.

De Libero, G. et al., "Self glycosphingolipids: new antigens recognized by autoreactive T lymphocytes," *News Physiol. Sci.* (2003) 18:71-76.

European Office Action for Application No. 03816701.1 dated Nov. 29, 2007.

European Office Action for Application No. 05810863.0 dated Apr. 2, 2008 (4 pages).

Feldman et al., Anti-TNFα Therapy Is Useful in Rheumatoid Arthritis and Crohn's Disease: Analysis of the Mechanism of Action Predicts Utility in Other Diseases, Transplantation Proceedings vol. 30, 1998, pp. 4126-4127.

Fischer, K. et al., "Mycobacterial phosphatidylinositol mannoside is a natural antigen for CD1d-restricted T cells," *Proc. Natl. Acad. Sci. USA* (2004) 101:10685-10690.

Fujii et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.* (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," *J. Clin. Invest.* (2004) 114(10):1379-1388.

Godfrey, D.I. et al., "The elusive NKT cell antigen—is the search over?" *Science* (2004) 306:1687-1688.

Goff, R.D. et al., "Effects of lipid chain lengths in alpha-galactosylceramides on cytokine release by natural killer T cells," *J. Am. Chem. Soc.* (2004) 126:13602-13603.

Goodman & Gilman's The Pharmacological Basis of Therapeutics, Tenth Edition, Hardman and Limbird, editors, The McGraw-Hill Companies, Inc., New York, (2001) 54-56.

Gui, M. et al., "TCR beta chain influences but does not solely control autoreactivity of V alpha 14J28IT cells," *J. Immunol.* (2001) 167(11):6239-6246.

Gumperz, J.E. et al., "Functional distinct subsets of CD1d-restricted natural killer T cells revealed by CD1d tetramer staining," *J. Exp. Med.* (2002) 195(5):625-636.

Gumperz, J.E. et al., "Murine CD1d-restricted T cell recognition of cellular lipids," *Immunity* (2000) 12:211-221.

Gupta, R.K. et al., "Adjuvants—a balance between toxicity and adjuvanticity," *Vaccine* (1993) 11(3):293-306.

Hashimoto, S. et al., "Glycosylation Using Glucopyranosyl Fluorides and Silicon-Based Catalysts, Solvent Dependency of the Stereoselection," *Tetrahedron Letters* (1984) 25:13:1379-1382.

Hayashi, M. et al., "Simple Synthesis of Glycosyl Fluorides," *Chem. Letters* (1984) 1747-1750.

Hermans, I.F. et al., "NKT cells enhance CD4+ and CD8+ T cell responses to soluble antigen in vivo through direct interaction with dendritic cells," *J. Immunol.* (2003) 171:5140-5147.

Honey, K. et al., "Thymocyte expression of cathepsin L is essential for NKT cell development," *Nat. Immunol.* (2002) 3:1069-1074.

Iida, N. et al., "A sulfated glucosylceramide from rat kidney," *J. Biol. Chem.* (1989) 264(10):5974-5980.

Islam, I. et al., "Synthesis and antiviral activity of (2-((4-(3-((1-methylethyl)amino)-2-pyridyl)-1-piperazinyl)carbony)-1H-indo 1-5-yl) (BHAP) acylspingosine HIV reverse transcriptase inhibitors," *Biorg Chem.* (1995) 23(4):499-511.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," *J. Immunol.* (2004) 172:1786-1800.

Karadimitris, A. et al., "Human CD1d-glycolipid tetramers generated by in vitro oxidative refolding chromatography," *Proc. Natl. Acad. Sci. USA* (2001) 98(6):3294-3298.

Kawano, T. et al., "CD1d-restricted and TCR-mediated activation of Vα14 NKT cells by glycosylceramides," *Science* (1997) 278:1626-1629.

Khan, M. et al., "Syntheses and Antiinflammatory Activity of Some 6-aryl-2,3,4,5-tetrahydro-3-pyridazinones," *Indian J. Chem.* (2000) 39B:614-619.

Kinjo, Y. et al., "Recognition of bacterial glycosphingolipids by natural killer T cells," *Nature* (2005) 434:520-525.

Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," *J. Exp. Med.* (1999) 189:1121-1127.

Ko et al. "α-Galactosylceramide Can Act As a Nasal Vaccine Adjuvant Inducing Protective Immune Responses against Viral Infection and Tumor." *Journal of Immunology.* vol. 175. No. 5. 2005. pp. 3309-3317.

Kronenberg, M., "Toward an understanding of NKT cell biology: progress and paradoxes," *Ann. Rev. Immunol* (2005) 23:877-900.

Laurence et al., "$T_H$-17 differentiation: of mice and men", Nature Immunology, vol. 8 No. 9, 2007, pp. 903-905.

Lee, P.T. et al., "Testing the NKT cell hypothesis on human IDDM pathogenesis," *J. Clin. Invest.* (2002) 110(6):793-800.

Lei et al., "Synthesis of a 3-Deoxy-L-iduronic Acid Containing Heparin Pentasaccharide to Probe the Conformation of the Antithrombin III Binding Sequence", Bioorganic & Medicinal Chemistry vol. 6, 1998, pp. 1337-1346.

(56) References Cited

OTHER PUBLICATIONS

Liu et al., "A modified alpha-galactosyl ceramide for staining and stimulating natural killer T cells." *Journal of Immunological Methods* vol. 312, Mar. 2006, pp. 34-39.

Long et al., "Synthesis and evaluation of stimulatory properties of *Sphingomonadaceae* glycolipds," *Nature Chemical Biology* (2007) 9: 559-564. XP002542183.

Matsuda, J.L. et al., "Tracking the response of natural killer T cells to a glycolipid antigen using CD1d tetramers," *J. Exp. Med.* (2000) 192(5):741-753.

Mattner, J. et al., "Exogenous and endogenous glycolipid antigens activate NKT cells during microbial infections," *Nature* (2005) 434:525-529.

Miyamoto, K. et al., "A Synthetic Glycolipid Prevents Autoimmune Encephalomyelitis by Inducing TH2 Bias of Natural Killer T Cells," *Nature* (2001) 413:531-534.

Morita, M. et al., "Structure-Activity Relationship of α-Galactosylceramides Against B16-Bearing Mice," *J. Med. Chem.* (1995) 38:2176-2187.

Nakagawa, R. et al., "Mechanisms of the Antimetastatic Effect in the Liver and of the Hepatocyte Injury Induced by α-Galactosylceramide in Mice," *J. Immun.* (2001) 166:11:6578-6584.

Pal, E. et al., "Costimulation-Dependent Modulation of Experimental Autoimmune Encephalomyelitis by Ligand Stimulation of Vα14 NK T Cells," *J. Immunol.* (2001) 166:662-668.

Park, S.H. et al., "CD1-restricted T-cell responses and microbial infection," *Nature* (2000) 406:788-792.

Park, S.H. et al., "The Mouse CD1d-restricted Repetoire is Dominated by a Few Autoreactive T cell Receptor Families," *J. Exp. Med.* (2001) 8:893-904.

Park, S.-H. et al., "Tissue-specific recognition of mouse CD1 molecules," *J. Immunol.* (1998) 160:3128-3134.

Petrovsky, N. et al., "Vaccine adjuvants: current state and future trends," *Immunol. Cell Biol.* (2004) 82:488-496.

Prigozy, T.I. et al., "Glycolipid antigen processing for presentation by CD1d molecules," *Science* (2001) 291:664-667.

Rock, K.L. et al., "Natural endogenous adjuvants," *Springer Semin. Immunopathol.* (2005) 26:231-24.

Sakai, T. et al., "Effects of α- and β-Galactosylated C2-Ceramides on the Immune System," *J. Med. Chem.* (1998) 41:650-652.

Sidobre, S. et al., "CD1d tetramers: a powerful tool for the analysis of glycolipid reactive T cells," *J. Immunol. Methods* (2002) 268:107-121.

Silk et al. "Utilizing the adjuvant properties of CD1d-dependent NK T cells in T cell-mediated immunotherapy." *Journal of Clinical Investigation*. vol. 114. No. 12. 2004. pp. 1810-1811.

Sinay, P. et al., *Bioorganic and Medicinal Chemistry* (1998) 6: 1337-46.

Singh et al., "The natural killer T Cell ligand Alpha-Galactosylceramide protects mice against EAE by an IL-4- and IL-10- dependent mechanism," *FASEB J., Fed. Of Amer. Soc. For Exp. Bio* (2002) 16: A1043.

Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," *Carbohydrate Res.* (1970) 12:261-266.

Smyth, M.J. et al., "NKT cells—conductors of tumor immunity?" *Curr. Opin. Immunol.* (2002) 14(2):165-171.

Smyth, M.J. et al., "NKT cells and tumor immunity—a double-edged sword," *Nature Immunology* (2001) 1:459-460.

Stanic A.K. et al., "Defective presentation of the CD1d1-restricted natural Va14Ja18 NKT lymphocyte antigen caused by Beta-D-glucosylceramide synthase deficiency," *Proc. Natl. Acad. Sci. USA* (2003) 100:1849-1854.

Supplementary Search Report of the European Patent Office for Application No. 03816701.1 dated Sep. 17, 2007.

Takikawa et al., "Diastereoselective Epoxidation of the Double Bond at C-4 of Sphingosines to Provide Phytosphingosine Relatives such as α-Galactosylceramide KRN7000," *Tetrahedron* (1998) 54:3141-3150.

The Merck Manual, 16th Edition (1999): pp. 339-342 and 1488-1490.

United States Office Action for U.S. Appl. No. 12/624,048 mailed Sep. 29, 2010.

United States Office Action for U.S. Appl. No. 10/550,165 mailed Oct. 27, 2008.

United States Office Action for U.S. Appl. No. 10/550,165 mailed Jan. 9, 2008.

United States Office Action for U.S. Appl. No. 10/550,165 mailed Jul. 20, 2007.

United States Office Action for U.S. Appl. No. 10/550,165 mailed Apr. 12, 2007.

Van Der Vliet, H.J.J. et al., "Effects of α-galactosylceramide (KRN7000), interleukin-12 and interleukin-7 on phenotype and cytokine profile of human Vα24+ Vβ11+T cells," *Immunology* (1999) 98:557-563.

Van Kaer, L., "Alpha-galactosylceramide therapy for autoimmune diseases: prospects and obstacles," *Nat. Rev. Immunol.* (2005) 5:31-42.

Vandommelen, S.L.H. et al., "Activation of natural killer (NK) T cells during murine cytomegalovirus infection enhances the antiviral response mediated by NK cells," *J. Virology* (2003) 77(3):1877-1884.

Vaultier, M. et al., "Reduction d'azides en amines primaires par une methode generale utilisant la reaction de staudinger," *Tetrahedron Letters* (1983) 24:763 (Not in English).

Wang, B. et al., "CD1-Restricted NK T Cells Protect Nonobese Diabetic Mice from Developing Diabetes," *J. Exp. Med.* (2001) 194:313-319.

Wang, F. et al., "Tuning of Binding Selectivity: Metal Control of Organic Guest Binding and Allosteric Perturbation of Fluorescent Metal Sensor," *J. Org. Chem.* (1999) 64:8922-8928.

Weber, G. et al., "Synthesis and Spectral Properties of a Hydrophobic Fluorescent Probe: 6-Propionyl-2-(dimethylamino) naphthalene," *Biochem.* (1979) 18:14:3075-3078.

Winau, F. et al., "Saposin C is required for lipid presentation by human CD1b," *Nat. Immunol.* (2004) 5:169-174.

Wu et al., "Bacterial glycolipids and analogs as antigen for CD1d-restricted NKT cells," *PNAS* (2005) 102(5):1351-1356.

Wu, D.Y. et al., "Cross-presentation of disialoganglioside GD3 to natural killer T cells," *J. Exp. Med.* (2003) 198:173-181.

Xia, C. et al., "Thio-isoglobotrihexosylceramide, an Agonist for activating invariant natural killer T cells," *Org. Lett.* (2006) 8(24):5493-5496.

Yu, K.O.A. et al., "Modulation of CD1d-restricted NKT cell responses by using N-acyl variants of alpha-galactosylceramides," *Proc. Natl. Acad. Sci. USA* (2005) 102(9):3383-3388.

Zajonc, D.M. et al., "Structural basis for CD1d presentation of a sulfatide derived from myelin and its implications for autoimmunity," *J. Exp. Med.* (2005) 202(11):1517-1526.

Zajonc, D.M. et al., "Structure and function of a potent agonist for the semi-invariant natural killer T cell receptor," *Nat. Immunol.* (2005) 6:810-818.

Zhou et al., "Synthesis and NKT cell stimulating properties of fluorophore-and biotin-appended 6"-amino-6"deoxy-galactosylceramides," *Org. Lett.* (2002) 4(8):1267-1270. XP003008968.

Zhou, D. et al., "Editing of CD1d-bound lipid antigens by endosomal lipid transfer proteins," *Science* (2004) 303:523-527.

Zhou, D. et al., "Lysosomal glycosphingolipid recognition by NKT cells," *Science* (2004) 306:1786-1789.

Zhou, D., "The immunological function of iGb3," Curr. Prot. Pept. Sci. (2006) 7:325-333.

International Search Report for Application No. PCT/US2005/031407. Sep. 8, 2006.

Written Opinion for Application No. PCT/US2005/031407. Mar. 3, 2007.

International Search Report for International Application No. PCT/US2007/072451. Nov. 27, 2007.

Written Opinion for International Application No. PCT/US2007/072451. Nov. 27, 2007.

International Search Report for International Application No. PCT/US06/002781. Dec. 20, 2006.

Written Opinion for International Application No. PCT/US06/002781. Dec. 20, 2006.

(56) References Cited

OTHER PUBLICATIONS

International Search Report for International Application No. PCT/US07/66250. Oct. 15, 2007.
Written Opinion for International Application No. PCT/US07/66250. Oct. 15, 2007.
International Search Report for International Application No. PCT/US03/08530. Aug. 3, 2004.
Written Opinion for International Application No. PCT/US03/08530. Jun. 30, 2005.
Supplemental European Search Report for EP Application No. 07760333.0 mailed Sep. 3, 2010.
Fuji et al., *Clinical Cancer Research*, vol. 6, No. 8, 2000, pp. 3380-3387.
Yamaguchi et al., *Oncology Research, Pergamon Press*, "Enhancing Effects of (2S, 3S, 4R)-1-0-0 Alpha-D-Galactopyranosyl)-2-(N-Hexacosanoylamino)-1, 3, 4-Octadecanetriol (KRN7000) on Antigen-Presenting Function of Antigen-Presenting Cells and Antimetastatic Activity of KRN7000-Pretreated Antigen-Presenting Cells.", Jan. 1996, vol. 8, No. 10-11, pp. 399-407.

\* cited by examiner

INCREASE OF IMMUNE RESPONSE AND TARGETING BY ANTIGENS AND/OR DRUG LINKAGE

This application is a National Stage Application of PCT/EP2008/065179, filed 7 Nov. 2008, which claims benefit of Serial No. 07291336.1, filed 7 Nov. 2007 in Europe and U.S. Ser. No. 60/996,226, filed 7 Nov. 2007 and which applications are incorporated herein by reference. To the extent appropriate, a claim of priority is made to each of the above disclosed applications.

The present invention relates to NKT cell activating glycolipids covalently bound to antigens and/or drug.

The present invention relates to compounds consisting of glycolipids covalently bound to an antigen or a drug via a linker. The said compounds are able to induce a stronger immune response than a composition comprising separated glycolipids and antigen. The said compounds are also able to target drug to CD1d restricted cells.

Natural killer T cells ("NKT cells") are a population of innate-like memory/effector cells that express both natural killer (NK) receptors and a conserved, semi-invariant T cell receptor (TCR). NKT cells have been implicated in suppression of autoimmunity and graft rejection, promotion of resistance to pathogens, and promotion of tumor immunity.

NKT cells respond with vigorous cytokine production within hours of TCR activation by releasing $T_{H1}$-type cytokines, including IFN-γ and TNF, as well as $T_{H2}$-type cytokines, including IL-4 and IL-13. The modulation of these lymphokine responses is the major intended effect of adjuvants used in immunogenic compositions.

NKT cells recognize foreign and self lipid antigens presented by the CD1d member of the family of β2 microglobulin-associated molecules. A variety of lipids with different structures have been shown to bind CD1d molecules in a unique manner that accommodates a fatty acid chain in each of the two hydrophobic binding pockets (A' and F) of the CD1d molecule. Lipid species capable of binding CD1d molecules include mycolic acids, diacylglycerols, sphingolipids, polyisoprenoids, lipopeptides, phosphomycoketides and small hydrophobic compounds.

A number of natural and synthetic lipid molecules are processed by antigen-presenting cells and presented by CD1 molecules to NKT cells. The prototypical compound used to study NKT cell activation in vitro and in vivo is KRN7000, and α-galactosyceramide ("αGalCer") derived from marine sponge *Agelas mauritianus*. Additional compounds recently identified include isoglobotrihexosylceramide ("iGB3") which is an endogenous glycolipid which was described in the PCT patent application WO2006/029010, and PBS-57, a modified 6"amino-6"deoxygalactosyceramide, which was described in PCT application PCT/US2007/066250, incorporated herein by reference. These compounds activate NKT cells and upregulate cytokine responses in vitro and in vivo. Accordingly, it has been proposed to use such compounds as adjuvant to improve vaccine efficacy when co-administered with an antigen (PCT patent application WO2006/083671).

In the context of vaccination, the antigen has to be presented by an antigen-presenting cell (APC), in particular dendritic cells (DCs), to the conventional CD8+ and CD4+ T cells through MHC class I or class II molecules respectively in order to induce a specific immune response towards this antigen. To this purpose, a reciprocal activation of NKT cells and dendritic cells is initiated upon the presentation of α-galactosylceramides by resting dendritic cells to NKT cells, inducing NKT cells to up-regulate CD40L and Th1 and Th2 cytokines and chemokines. Then CD40 cross-linking induces dendritic cells to upregulate CD40, B7.1 and B7.2 and IL-12, which in turn enhances NKT cell activation and cytokine production. Propagation of this reaction involves the activation of NK cell cytolysis and IFN-γ production, and, most importantly, the up-regulation of dendritic cells co-stimulating properties and MHC class I- and MHC class II-mediated antigen presentation.

Glycolipids, linked directly to a reporter group such as a fluorophore or other small molecule (e.g., biotin), have been proposed as probes for observing glycolipid association with CD1d and NKT cells (PCT patent application WO2004/094444). In particular, fluorophore and biotin appended 6"amino-6"deoxy-galactosylceramide have been used to understand the roles of glycolipid structure in CD1d and NKT cell receptor binding. The staining allowed observation of the trafficking of glycolipids and the quantification of their association with CD1d and NKT cell receptors (Zhou et al., Org. Lett. 2000 4:1267-1270). Dansyl-, prodan derivative, and biotin-appended 6"-amino-6"-deoxy-galactosylceramides were found to stimulate NKT cells similarly to the parent glycolipid, suggesting that these compounds go through endocytosis, CD1d loading, presentation on the cell surface, and binding to T cell receptors causing T cell stimulation. However, Zhou et al. appended small molecules to the glycolipid for labelling NKT cells and/or CD1d restricted cells. It remains unknown if addition of larger molecules on the lipid chain would interfere with binding to CD1d. Furthermore, glycolipids bound with antigens or drugs have not been reported so far.

DESCRIPTION OF THE INVENTION

Surprisingly, the inventors have found that a compound consisting of a glycolipid covalently bound to an antigen via a linker is able to trigger a specific immune response against the antigen stronger than the response observed when the glycolipid and the antigen are separately co-administered in a composition.

Not to be bound by theory, it is assumed that, upon the co-delivery of the antigen and the NKT agonist to the same APC, preferably the same B lymphocyte or the same DC, the B cell and/or DC becomes activated by the NKT cell and the antigen will therefore be presented to the conventional T cells by a fully activated B cell and/or DC. The proximity of an activated NKT may be useful when the APC presents antigen to a T cell, since it will contribute to the cytokine environment.

Additionally, when the glycolipid is covalently bound to a drug, the glycolipid enables for specific targeting of the drug to NKT cells.

The present invention thus relates to compounds consisting of glycolipids covalently bound via a linker to an antigen or a drug, and to uses thereof.

Compound Consisting of Glycolipid Covalently Bound Via a Linker to an Antigen or Drug The compounds of the invention have Formula (I)

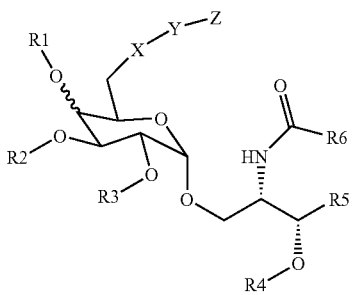

wherein, $R_1$, $R_2$, $R_3$, and $R_4$ are each independently hydrogen, $C_1$-$C_6$ alkyl, $C_6$-$C_{12}$ aralkyl, or $C_1$-$C_6$ acyl; and $R_1$ is either above or below the sugar ring.

$R_6$ is a) —$(CH_2)_xCH_3$ where x is an integer selected from 1 to 100; or b) —$(CH_2)_xCH=CH(CH_2)_yCH_3$ or —$(CH_2)_xCH=CH(CH_2)_yCH=CH(CH_2)_zCH_3$ wherein x, y and z are integers independently selected from 1 to 14.

$R_5$ is one of the following formulae (II), (III) or (IV)

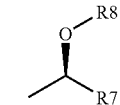

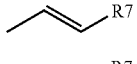

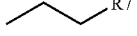

wherein $R_8$ is hydrogen, $C_1$-$C_6$ alkyl, $C_6$-$C_{12}$ aralkyl, or $C_1$-$C_6$ acyl, and $R_7$ is a linear or branched $C_3$-$C_{100}$ alkyl;

X is O, N or S;

Y is a cleavable or non-cleavable linker group; and

Z is an antigen or a drug or a pharmaceutically acceptable salt thereof.

As used herein, the term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The terms "arylalkyl" or "aralkyl" refer to an alkyl moiety in which an alkyl hydrogen atom is replaced by an aryl group. Examples of "arylalkyl" or "aralkyl" include benzyl and 9-fluorenyl groups.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "cycloalkyl" as employed herein includes saturated cyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclohexyl and adamantyl.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl.

The term "heterocyclyl" refers to a non-aromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e. g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e. g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "oxo" refers to an oxygen atom, which forms a carbonyl when attached to carbon, an N-oxide when attached to nitrogen, and a sulfoxide or sulfone when attached to sulfur.

The term "substituents" refers to a group "substituted" on an alkyl, cycloalkyl, heterocyclyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl.

$R_6$ can have 1 to 100 methylene ($CH_2$) groups (i.e. $R_6$ is $(CH_2)_xCH_3$ and x=1-100). In particular $R_6$ may have 1-75 $CH_2$ groups, 1-50 $CH_2$ groups, 1-25 $CH_2$ groups, 1-20 $CH_2$ groups, 1-15 $CH_2$ groups, 1-10 $CH_2$ groups or 1-5 $CH_2$ groups. Preferably, $R_6$ has 15-25 $CH_2$ groups. More preferably, $R_6$ has 20-25 $CH_2$ groups.

In certain embodiments $R_6$ contains 22 or 24 $CH_2$ groups (x=22 or x=24).

$R_7$ may be in particular a linear or branched $C_3$-$C_{75}$ alkyl, $C_3$-$C_{50}$ alkyl, $C_3$-$C_{25}$ alkyl, $C_3$-$C_{20}$ alkyl, $C_3$-$C_{15}$ alkyl, $C_{10}$-$C_{15}$ alkyl or $C_3$-$C_{10}$ alkyl.

In certain embodiments $R_7$ is an unbranched alkyl group of 14 carbon atoms.

Preferably $R_6$ is $C_{25}H_{51}$ and $R_7$ is $C_{14}H_{29}$. More preferably, $R_6$ is $C_{23}H_{45}$ and $R_7$ is $C_{14}H_{29}$. In another preferred embodiment, $R_6$ is $C_{23}H_{47}$ and $R_7$ is $C_{14}H_{29}$.

When $R_1$-$R_3$ are other than hydrogen, preferably each are independently methyl, benzyl or acetyl.

According to an embodiment (referred thereafter as PBS-6), $R_1$, $R_2$, $R_3$, $R_4$ and $R_8$ are hydrogen, $R_5$ is (II), $R_6$ is $C_{25}H_{51}$, $R_7$ is $C_{14}H_{29}$ and X is N.

According to another embodiment (referred thereafter as PBS-57), $R_1$, $R_2$, $R_3$, $R_4$ and $R_8$ are hydrogen, $R_5$ is (II), $R_6$ is $C_{23}H_{45}$, $R_7$ is $C_{14}H_{29}$ and X is N.

According to still another embodiment (referred thereafter as PBS-14), $R_1$, $R_2$, $R_3$, $R_4$ and $R_8$ are hydrogen, $R_5$ is (II), $R_6$ is $C_{25}H_{51}$, $R_7$ is $C_{14}H_{29}$ and X is N.

In another embodiment (referred thereafter as PBS-96), $R_1$, $R_2$, $R_3$, $R_4$ and $R_8$ are hydrogen, $R_5$ is (II), $R_6$ is $C_{23}H_{47}$, $R_7$ is $C_{14}H_{29}$ and X is N.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e. g., magnesium), ammonium and $N\text{-(alkyl)}_4^+$ salts. This invention also envisions the quaternization of any basic nitrogen-containing groups of the compounds disclosed herein. Water or oil-soluble or dispersible products may be obtained by such quaternization. Salt forms of the compounds of the formula herein can be amino acid salts of carboxy groups (e.g., L-arginine, -lysine, -histidine salts).

The glycolipid moiety of the compounds according to the invention described above may be synthesized as disclosed in the International patent application WO2004/094444 which is incorporated herein by reference.

Coupling of the linker-antigen or drug moiety (Y—Z) on the glycolipid moiety may be performed according to the method described in Zhou et al. (Org. Lett. 2000 4:1267-1270).

An example of peptide antigen conjugation is displayed on the following scheme I:

Scheme I

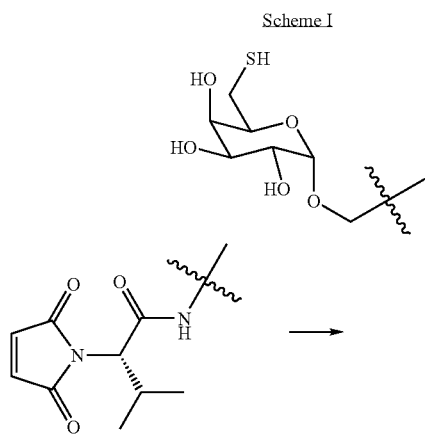

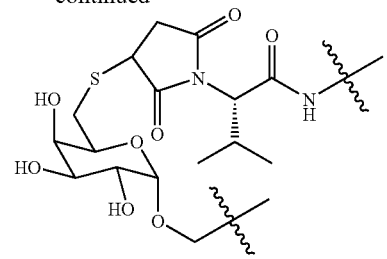

For obtaining such a peptide antigen conjugation, the peptide can be dissolved at 50-100 μM in a suitable buffer at pH 7.0-7.5 at room temperature. Reduction of the disulfide bonds in the peptide can be carried out by adding a 10-fold molar excess of a reducing agent such as DTT or TCEP. The glycolipid containing the reactive group can be added dropwise to the peptide solution while stirring, to a final ratio of 10-20 moles of glycolipid for each mole of peptide. The reaction can be allowed to proceed for 2 hours at room temperature or overnight at 4° C. The conjugate can finally be separated on a ge I filtration column.

The linker group Y can be any carbon-containing chain or ring. For example, the linker can be —$(CH_2)_t$—, in which the chain optionally contains one or more terminal heteroatoms (e.g., N, O, S), and/or one or more heteroatoms, rings, double bonds, triple bonds that are inserted into the chain. The value of "t" can be 1-20, preferably 3-10.

In a preferred embodiment of the present invention, the linker is composed of 6 carbons.

Preferably, the linker contains a proteolytic cleavage site, in particular an endo-lysosomal protease cleavage site. Alternatively, the linker group contains a lipase cleavage site. In particular, the linker group may contain a protease cleavage site and/or a lipase cleavage site.

Preferably, the compound according to the present invention is capable of binding a CD1d monomer or tetramer. More preferably, this compound is able to activate an NKT cell.

As used herein, an "antigen" refers to any substance or material that is specifically recognized by a binding entity of the immune system, such as an antibody or antibody fragment comprising the paratope or a T cell receptor (TCR).

Suitably, antigens of the compound of Formula (I) are derived from attenuated or killed infectious agents. Whole microorganisms or portions thereof (e.g., membrane ghosts; crude membrane preparations, lysates and other preparations of microorganisms) may be used. Suitable infectious agents from which an antigen may be derived include, but are not limited to, pathogens and microorganisms such as bacteria, parasites and viruses. In some contexts, suitable antigens are obtained or derived from a viral pathogen that is associated with human disease including, but not limited to, HIV/AIDS (Retroviridae, e.g., gp120 molecules for HIV-1 and HIV-2 isolates, HTLV-I, HTLV-11), influenza viruses (Orthomyxoviridae, e.g., types A, B and C), herpes (e.g., herpes simplex viruses, HSV-1 and HSV-2 glycoproteins gB, gD and gH), rotavirus infections (Reoviridae), respiratory infections (parainfluenza and respiratory syncytial viruses), Poliomyelitis (Picornaviridae, e.g., polioviruses, rhinoviruses), measles and mumps (Paramyxoviridae), Rubella (Togaviridae, e.g., rubella virus), hepatitis (e.g., hepatitis viruses types A, B, C, D, E and/or G), cytomegalovirus (e.g., gB and gH), gastroenteritis (Caliciviridae), Yellow and West Nile fever (Flaviviridae), Rabies (Rhabdoviridae), Korean hemorrhagic fever (Bunyaviridae), Venezuelan fever (Arenaviridae), warts (Papillomavirus), simian immunodeficiency virus, encephalitis virus, varicella zoster virus, Epstein-Barr virus, and other virus families, including Coronaviridae, Birnaviridae and Filoviridae.

Suitable bacterial and parasitic antigens can also be obtained or derived from known agents responsible for diseases including, but not limited to, diphtheria, pertussis, tetanus, tuberculosis, bacterial or fungal pneumonia, otitis media, gonorrhea, cholera, typhoid, meningitis, mononucleosis, plague, shigellosis or salmonellosis, Legionnaires' disease, Lyme disease, leprosy, malaria, hookworm, Onchocerciasis, Schistosomiasis, Trypanosomiasis, Leishmaniasis, giardiases, amoebiasis, filariasis, Borrelia, and trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Additional specific pathogens from which antigens can be derived include *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Francisella tularensis, Helicobacter pylori, Leptospira interrogans, Legionella pneumophila, Yersinia pestis, Streptococcus* (types A and B), *pneumococcus, meningococcus, Haemophilus influenza* (type b), *Toxoplasma gondii, Moraxella catarrhalis, donovanosis*, and *actinomycosis*; fungal pathogens include candidiasis and aspergillosis; parasitic pathogens include *Taenia*, flukes, roundworms, amebiasis, giardiasis, *Cryptosporidium, Schistosoma, Pneumocystis carinii, trichomoniasis* and *trichinosis*. The present invention can also be used to provide a suitable immune response against numerous veterinary diseases, such as foot-and-mouth diseases, coronavirus, *Pasteurella multocida, Helicobacter, Strongylus vulgaris, Actinobacillus pleuropneumonia*, Bovine Viral Diarrhea Virus (BVDV), *Klebsiella pneumoniae, Escherichia coli*, and *Bordetella pertussis, parapertussis* and *brochiseptica.*

In other embodiments, antigens for binding to glycolipids that may be used are tumor-derived antigens or autologous or allogeneic whole tumor cells. Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include cdk4 (melanoma), β-catenin (melanoma), caspase-8 (squamous cell carcinoma), MAGE-1 and MAGE-3 (melanoma, breast, glioma), tyrosinase (melanoma), surface Ig idiotype (e.g., BCR) (lymphoma), Her-2/neu (breast, ovarian), MUC-1 (breast, pancreatic) and HPV E6 and E7 (cervical carcinoma). Additional suitable tumor antigens include prostate specific antigen (PSA), sialyl Tn (STn), heat shock proteins and associated tumor peptides (e.g., gp96), ganglioside molecules (e.g., GM2, GD2, and GD3), carcinoembryonic antigen (CEA) and MART-1.

According to another embodiment, a drug is appended to the glycolipid. Examples of suitable drugs include cyclosporine, FK 506, and rapamycin Vaccine and Pharmaceutical Compositions Another aspect of this invention relates to a vaccine composition that comprises a compound of Formula (I) as defined above wherein Z is an antigen.

"Vaccine" refers to a composition which, when administered to a subject, induces cellular and/or humoral immune responses as described herein.

In the context of the invention, "subject" refers to an animal, preferably a non-human or human mammal. Examples of non-human mammals include rodents and primates. Most preferably, a subject is human.

The invention also provides a method of inducing, in particular stimulating, an immune response in a subject which comprises administering the subject with said compound or vaccine composition according to the invention.

In the context of the invention, "stimulating an immune response" refers to reinforcing an immune response which has been induced by the presence of an antigen.

In a preferred embodiment, the immune response is a humoral immune response. As used herein, a "humoral immune response" is the production of antibodies by B cells, and the accessory process that accompanies it, including, but not limited to, e.g., Th2 activation and cytokine production, germinal center formation and isotype switching, affinity maturation production and memory cell generation. For purposes of determining whether a humoral immune response is stimulated, a quantitative comparison of the signal in a sample from a subject vaccinated with the compound or vaccine composition defined above can be compared to a sample from a subject vaccinated with antigen alone. The humoral immune response may be evaluated by measuring the effector functions of antibodies, including pathogen or toxin neutralization, classical complement activation, and opsosin promotion of phagocytosin and pathogen elimination. The antibodies produced in response to administering the compound or vaccine composition defined above and an antigen may be of any type, e.g., IgM, IgA, or IgG. The humoral immune response may be assayed by any quantitative method known in the art, e.g., ELISA, single radial immunodiffusion assay (SRID), enzyme immunoassay (EIA), or hemagglutination inhibition assay (HAI).

In another preferred embodiment, the stimulation of an immune response corresponds to activation of CD4+ T lymphocytes. As understood in the art, CD4+ T cells, or "T helper cells," are cells that recognize antigens presented by class II major histocompatability marker (MHC) on the surface of antigen presenting cells, and secrete lymphokines to stimulate both cell-mediated and antibody-mediated branches of the immune system. CD4+ T cell activation promotes lymphokine secretion, immunoglobulin isotype switching, affinity maturation of the antibody response, macrophage activation and enhanced activity of natural killer (NK) and cytotoxic T cells (CTL). Lymphokines are proteins secreted by lymphocytes that affect their own activity and/or the activity of other cells. Lymphokines include, but are not limited to, interleukins and cytokines, e.g., IL-2, IL-4, IL-5, IL-6, IL-10, IL-12, or INFγ. For purposes of determining whether a CD4+ T lyphocytes are activated, a quantitative comparison of the signal in a sample from a subject vaccinated with the compound or vaccine composition as defined above can be compared to a sample from a subject vaccinated with antigen alone. Methods to assay activation CD4+ T cells are known in the art.

In another preferred embodiment, the stimulation of an immune response corresponds to activation of CD8+ T lymphocytes. CD8+ T lymphocytes recognize antigens presented by Class I MHC molecules (present on all nucleated cells). Engagement of the MHC class-I peptide complex results in delivery of lytic granules to the target cell causing lysis of the target cell. Methods used to assay the activation of CD8+ T cells are known in the art, and induce but are not limited to ELISPOT, ELISA, and cytotoxic assays. Alternatively, a mouse model may be used to monitor the activation of CD8+ T cells using a fluorescent assay to measure cell-mediated cytotoxicity, as described in Hermans et al. (2004) *J. Immunol. Meth.* 285:25-40.

Suitable effective dosage amounts of the compound of Formula (I) in vaccine compositions may be determined by those of skill in the art, but typically range from about 1 microgram to about 10,000 micrograms per kilogram of body weight, although they are typically about 1,000 micrograms or less per kilogram of body weight. In some embodiments, the effective dosage amount ranges from about 10 to about 5,000 micrograms per kilogram of body weight. In another embodiment, the effective dosage amount ranges from about 50 to about 1,000 micrograms per kilogram of body weight. In another embodiment, the effective dosage amount ranges from about 75 to about 500 micrograms per kilogram of body weight. The composition can be administered in a single dose, or split into multiple doses over a period of weeks or months. It will be appreciated that the dosage of antigen will depend on the specific antigen, and on the age and immune status of the subject, as well as other relevant factors that may be determined by those skilled in the art.

Administration of a vaccine of the invention may suitably result in therapeutic or prophylactic treatment of an infectious disease or a disease related to an infectious agent. "Treating" or "treatment" of an infectious disease includes one or more of: (1) inhibiting infection, i.e. preventing the infectious agent from establishing an infection, (2) preventing spread of the infectious agent, i.e. to other areas of the subject, or from one subject to another, (3) limiting disease severity, (4) preventing recurrent infections, i.e. limiting reactivation of latent or persistent infections, and (5) palliating symptoms of the infectious disease.

Another aspect of this invention relates to a pharmaceutical composition that contains a compound of Formula (I) wherein Z is a drug.

The invention also provides a method of treatment of a subject in need thereof which comprises administering said subject with said compound or pharmaceutical composition.

"An effective amount" refers to an amount of a compound that confers a therapeutic effect on the treated subject. The therapeutic effect may be objective (i.e., measurable by some test or marker) or subjective (i.e., subject gives an indication of or feels an effect). An effective amount of the compound described above may range from about 0.01 µg/Kg to about 500 µg/Kg, alternatively from about 0.1 to about 100 µg/Kg, alternatively from about 1 to about 50 µg/Kg. Effective doses will also vary depending on route of administration, as well as the possibility of co-usage with other agents.

As appreciated by skilled artisans, vaccines are suitably formulated to be compatible with the intended route of administration. Examples of suitable routes of administration include parenteral, e.g., intravenous, intradermal, subcutaneous, intramuscular, oral (e.g., inhalation), transdermal (topical), transmucosal, and rectal administration.

Preferably, the vaccines according to the invention may be administered intramuscularly, intravenously, subcutaneously, intradermally, intraperitinatally, intranasally, enterally or by inhalation. Most preferably, the vaccines according to the invention are administered intramuscularly or subcutaneously.

The vaccine may also include a physiologically acceptable vehicle. A "physiologically acceptable" vehicle is any vehicle that is suitable for in vivo administration (e.g., oral, transdermal or parenteral administration) or in vitro use, i.e., cell culture. Suitable physiologically acceptable vehicles for in vivo administration include water, buffered solutions and glucose solutions, among others. Additional components of the compositions may suitably include excipients such as stabilizers, preservatives, diluents, emulsifiers or lubricants, in addition to the physiologically acceptable vehicle. In particular, suitable excipients include, but are not limited to, Tween 20, DMSO, sucrose, L-histadine, polysorbate 20 and serum.

The compounds of the formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 µg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions delineated herein include the compounds of the formula delineated herein, as well as additional therapeutic agents if present, in amounts effective for achieving a modulation of disease or disease symptoms, including those described herein.

The term "pharmaceutically acceptable carrier" refers to a carrier that may be administered to a patient, together with a compound of this invention, and which does not destroy the pharmacological activity thereof and is non-toxic when administered in doses sufficient to deliver a therapeutic amount of the compound.

Pharmaceutically acceptable carriers and vehicles that may be used in the pharmaceutical compositions of this invention include, but are not limited to, ion exchangers, alumina, aluminium stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formula described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension.

This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch.

Lubricating agents, such as magnesium stearate, are also typically added. For oral administration in a capsule form, useful diluents include lactose and dried corn starch.

When aqueous suspensions and/or emulsions are administered orally, the active ingredient may be suspended or dissolved in an oily phase is combined with emulsifying and/or suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents.

Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formula herein can be administered using an implantable device.

Implantable devices and related technology are known in the art and are useful as delivery systems where a continuous or timed-release delivery of compounds or compositions delineated herein is desired. Additionally, the implantable device delivery system is useful for targeting specific points of compound or composition delivery (e.g., localized sites, organs) (see Negrin et al., (2001) *Biomaterials*, 22 (6): 563).

Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic compounds herein. A patch includes a material layer (e.g., polymeric, cloth, gauze, bandage) and the compound of the formula herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

EXAMPLES

Example 1

Figure 1:
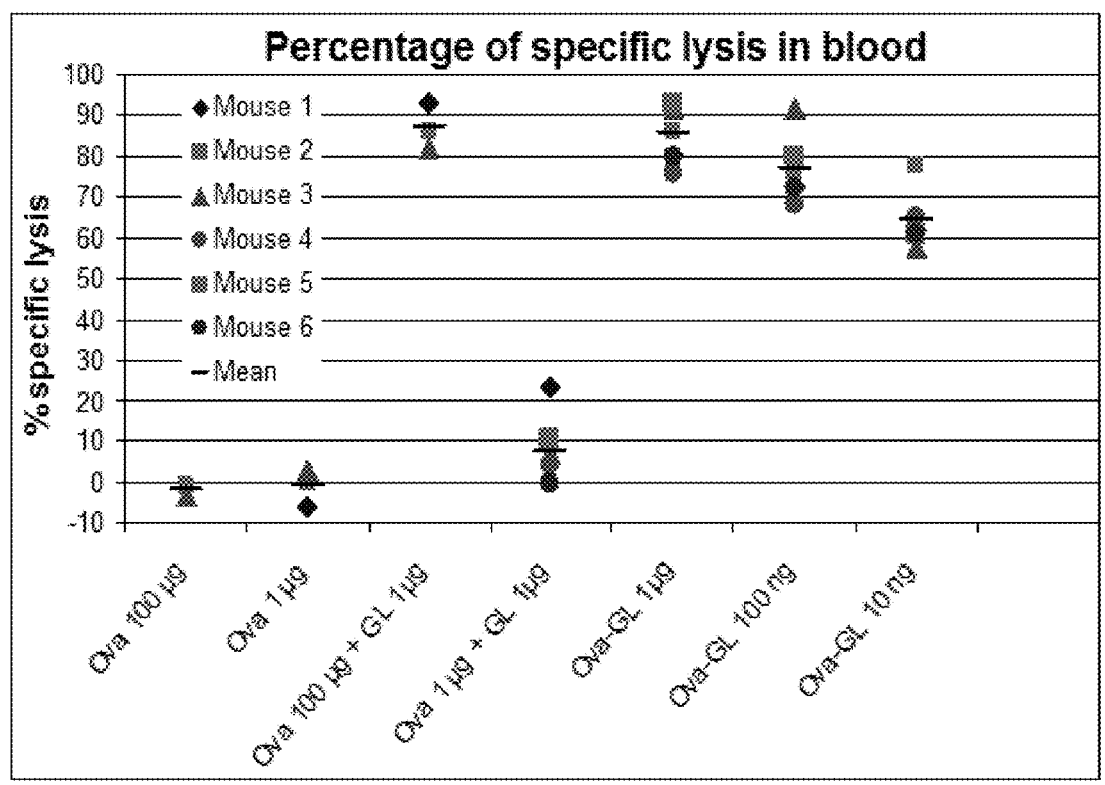
FIG. 1 shows the detection of SIINFEKL-specific cytolytic activity in blood of immunized mice. All samples have been collected the day after target cells injection. The mice were immunized by intravenous route with 100 µg of Ova peptide alone (group 1), 1 µg of Ova peptide alone (group 2), a combination of 100 µg of Ova peptide and 1 µg of glycolipid (group 3), a combination of 1 µg of Ova peptide and 1 µg of glycolipid (group 4), 1 µg of Ova peptide covalently linked to glycolipid (group 5), 100 ng of Ova peptide covalently linked to glycolipid (group 6) or 10 ng of Ova peptide covalently linked to glycolipid (group 7).

Test Immunization Induced with Antigen Linked with PBS6 Administrated by Intravenous Route in VITAL Assay Material Thirty-three 8 week-old C57Bl/6J CD45.2 female mice were used for immunisation. They were split into 8 groups: groups 1, 2, 4, 6 and 8 included 3 animals and groups 3, 5 and 7 included 6 animals.

Twenty 8 week-old C57Bl/6J CD45.2 female mice were used for target cells.

Target Cells for In Vivo Cytotoxicity Assay

The in vivo cytotoxicity of the ovalbumine peptide of sequence SIINFEKL (SEQ ID NO:1) (or Ova peptide) induced CD8+ T cell response was evaluated by VITAL assay as described by Hermans et al (2004, *J. Immunol. Methods*, 285:25-40). Briefly, congenic splenocyte populations were labelled with the fluorescent dye CFSE with either low concentration (0.6 µM during 10 min at 37° C.) or high concentration (6 µM during 10 min at 37° C.). Population labelled with high concentration of CFSE was pre-loaded with SIINFEKL peptide (5 µM during 60 min at 37° C.) whereas population labelled with low concentration of CFSE was pre-loaded with irrelevant LCMV gp33-41 peptide (5 µM during 60 min at 37° C.).

Equal numbers of both populations were mixed and injected by intra-venous route into immunized mice. $10 \cdot 10^6$ cells of each condition (total of $20 \cdot 10^6$ cells) in a volume of 100 µl were injected into the orbital sinus or into the lateral vein tail of each immunized mouse, 10 days after vaccination.

Treatment of Vaccination

The ovalbumine peptide consists in the SIINFEKL sequence (SEQ ID NO:1) (i.e. amino-acids 257-264 of ovalbumine) and the glycolipid used is PBS-6.

The mice were vaccinated by intravenous route at day 0 with 50 µl of the following solutions according to the different groups:

1-100 µg of Ova peptide into 50 µl of PBS
2-1 µg of Ova peptide into 50 µl of PBS
3-100 µg of Ova peptide combined with 1 µg of PBS-6 into 50 µl of PBS
4-1 µg of Ova peptide combined with 1 µg of PBS-6 into 50 µl of PBS
5-1 µg of Ova peptide covalently linked to PBS-6 into 50 µl of PBS
6-100 ng of Ova peptide covalently linked to PBS-6 into 50 µl of PBS
7-10 ng of Ova peptide covalently linked to PBS-6 into 50 µl of PBS Read Out Specific lysis of the SINFEKL-loaded targets was monitored by FACS analysis into peripheral blood cells or splenocytes. Blood samples have been collected into orbital sinus and spleens have been collected after immune mice sacrifice by day 11. The mean percent survival of peptide-pulsed targets was calculated relative to that of the control population, and cytotoxic activity was expressed as percent specific lysis (100 minus the mean percent survival of peptide-pulsed targets).

Results

The aim of this study was to evaluate a covalent linkage of peptide with glycolipid NKT agonist to induce specific lysis response when it was administered by intravenous route, compared to the same peptide mixed with the same glycolipid. Mice treated with 1 µg to 100 µg of Ova peptide alone presented no antigen-specific lysis. Baseline of natural lysis in placebo control was evaluated between −6% and +3% (FIG. 1). Results in mice treated with 100 µg of Ova peptide in combination with 1 µg of PBS6 by intravenous route presented strong specific lysis in all mice as expected. Mice treated with 1 µg of Ova peptide in combination with 1 µg of PBS-6 did not present any specific lysis after immunization by intravenous route. However, results in mice treated with 1 µg of Ova peptide covalently linked to PBS-6 presented strong specific lysis in all mice. This activity was still present at 100 and 10 ng. This result suggested that immunization by intravenous route with covalently linked antigenic peptide gave better result than the injection of the mixture.

In conclusion this experiment suggested that this linkage between antigen and CD1d restricted adjuvant increase the potency of the response.

Example 2

Evaluation of the Stimulation of the Immune Response Induced by Glycolipid Adjuvant Using the Model Antigen OVA Material Forty-eight 9 week-old C57Bl/6J CD45.2 female mice were used for immunisation. They were split into 9 groups: groups 1 and 2 included 3 animals and groups 3 to 9 included six animals.

Treatment of Vaccination:

The ovalbumin peptide consists in the VSGLEQLESIIN-FEKLTEWTS sequence (SEQ ID NO:2) and the glycolipids used are PBS-6, PBS-14 and PBS-57.

The mice were vaccinated by intramuscular route at day 0 and 14 with the following solutions according to the different groups:

Group 1: 100 µl of PBS;
Group 2: 50 µg of Ova into 100 µl of PBS;
Group 3: 1 µg of Ova-PBS-6 into 100 µl of PBS;
Group 4: 1 µg of Ova-PBS-14 into 100 µl of PBS;
Group 5: 1 µg of Ova-PBS-57 into 100 µl of PBS.
Read Out:
Detection of SIINFEKL specific CD8+ cells was monitored by FACS following H-2 Kb SIINFEKL pentamer and CD8 co-staining.

Cytokine response was monitored in the spleen by CBA analysis. Cytokine secretion was monitored with the Mouse Th1/Th2 cytokine CBA on Flow cytometer, and cytokine concentration determined using the FCAP Array software, BD.

Results

The aim of this study was to evaluate the efficacy of the linkage between an antigen and a glycolipid to induce specific immune responses when it was administered by intramuscular route.

Figure 2:
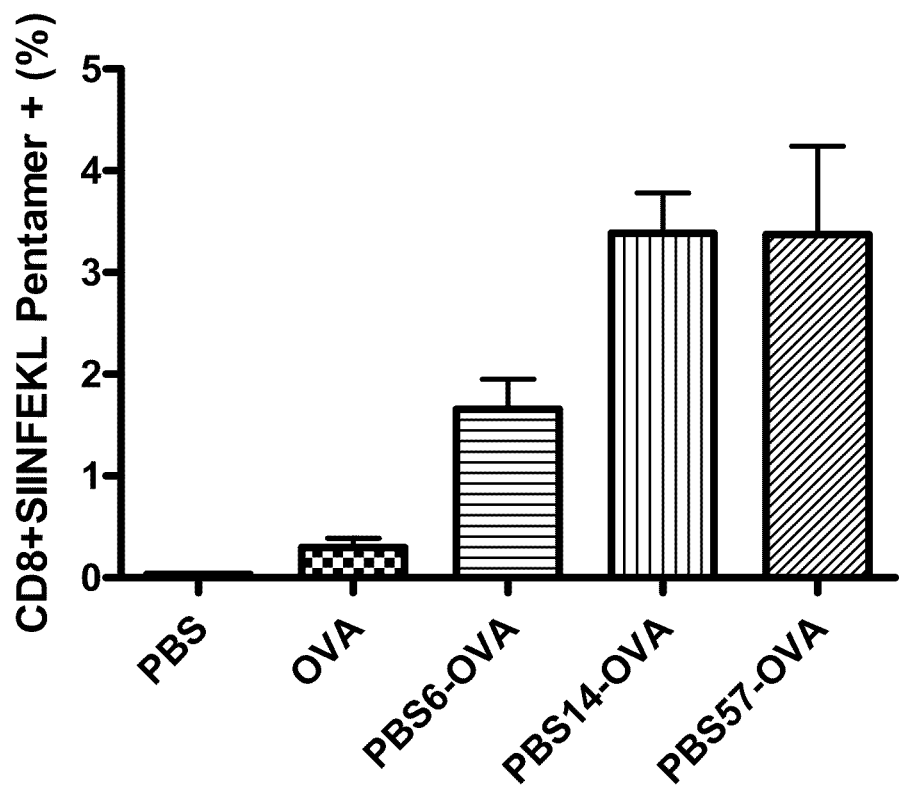
FIG. 2 shows histograms representing the percentage of SIINFEKL-H2K$^b$ specific CD8+ (CD8+ SIINFEKL Pentamer+(%), abscissa) in the blood from mice immunized with PBS (PBS), ovalbumin peptide (OVA), ovalbumin peptide covalently linked to PBS-6 (PBS6-OVA), ovalbumin peptide covalently linked to PBS-14 (PBS14-OVA), or ovalbumin peptide covalently linked to PBS-57 (PBS57-OVA).

Mice treated with 1 µg of OVA covalently linked to either PBS-6, PBS-14 or PBS-57, presented a stronger percentage of SIINFEKL-H2K$^b$ specific CD8$^+$ in the blood than mice treated with 50 µg of OVA alone (FIG. 2).

Accordingly, this experiment demonstrates that the linkage between antigen and glycolipid adjuvants increase the potency of the response.

Example 3

Test Immunization Induced with Antigen Linked with Different Glycolipid Adjuvants Administrated by Intramuscular Route Material Sixty-nine 9 week-old C57Bl/6J CD45.2 female mice were used for immunisation. They were split into 14 groups: groups 1 to 5 included 3 animals, and groups 6 to 14 included 6 animals.

Target Cells for In Vivo Cytotoxicity Assay

The in vivo cytotoxicity of SIINFEKL (SEQ ID NO:1) induced CD8$^+$ T cell response was evaluated by VITAL assay as described in Example 1.

Treatment of Vaccination

The short ovalbumin peptide consists in the SIINFEKL sequence (SEQ ID NO:1; amino acids 257 to 264 of ovalbumin), the long ovalbumin peptide consists in the VSGLEQLESIINFEKLTEWTS sequence (SEQ ID NO:2; amino acids 250 to 269 of ovalbumin) and the glycolipids used are PBS-6, PBS-14 and PBS-57.

The mice were vaccinated by intramuscular route at day 0 with the following solutions according to the different groups:

Group 1: 50 µl of PBS;
Group 2: 50 µg of Short OVA into 50 µl of PBS/DMSO;
Group 3: 50 µg of Long OVA into 50 µl of PBS/DMSO
Group 4: 1 µg of PBS-6-OVA into 50 µl of PBS;
Group 5: 1 µg of PBS-57-OVA into 50 µl of PBS;
Group 6: 1 µg of PBS-14-OVA into 50 µl of PBS.
Read Out:
The read out was as described in Example 1.
Results The aim of this study was to evaluate a covalent linkage of peptide with glycolipid NKT agonist to induce specific lysis response when it was administrated by intramuscular route, compared to the same peptide alone.

Figure 3:
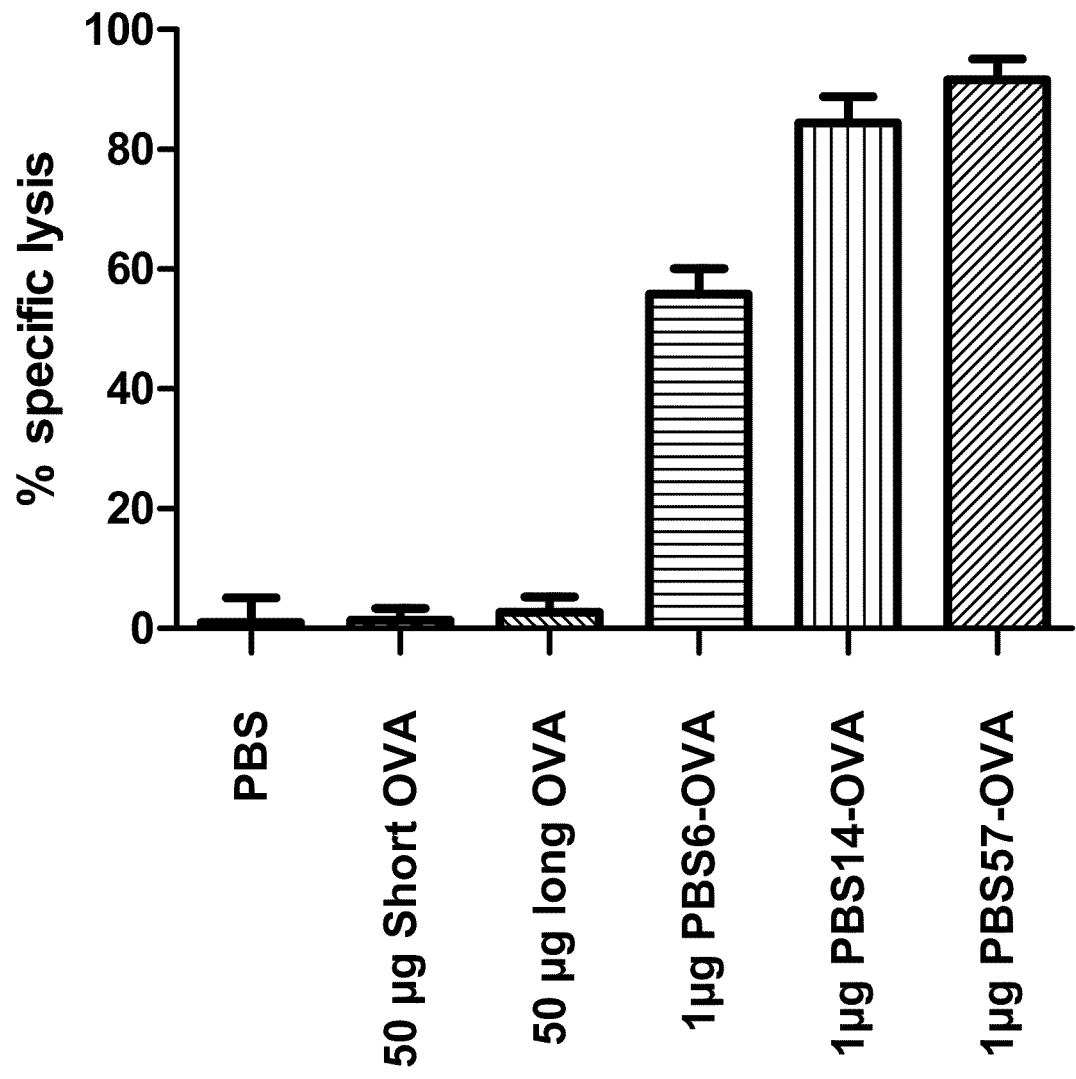
FIG. 3 shows histograms representing the percentage of SIINFEKL specific cytolytic activity (% specific lysis, abscissa) in the blood from mice immunized with PBS (PBS), short ovalbumin peptide (50 µg short OVA), long ovalbumin peptide (50 µg long OVA), ovalbumin peptide covalently linked to PBS-6 (1 µg PBS6-OVA), ovalbumin peptide covalently linked to PBS-14 (1 µg PBS14-OVA), or ovalbumin peptide covalently linked to PBS-57 (1 µg PBS57-OVA).

Mice treated with 1 µg of OVA covalently linked to either PBS-6, PBS-14 or PBS-57, presented a stronger percentage of SIINFEKL-specific cytolytic activity in the blood than mice treated with 50 µg of OVA alone (FIG. 3).

Accordingly, this experiment demonstrates that the linkage between antigen and glycolipid adjuvants increase the potency of the response.

Example 4

Evaluation of Specific Antibody Response Against Ovalbumin Peptide

The aim of this study was to evaluate IgG1 and IgG2a antibody response following immunization with ovalbumin in combination with different adjuvant covalently linked.

Material and Methods

The sera tested were as follows:
Group 1; 6 mice immunized with 500 µg of ova protein with CFA/IFA (Positive control)
Group 2: 6 mice immunized with 50 µg of long ova peptide of sequence ISSAESLKISQAVHAAHAEINEA (SEQ ID NO:3; amino acids 316 to 338 of ovalbumin)

Group 3: 6 mice immunized with 50 μg of short ova peptide of sequence KISQAVHAAHA (SEQ ID NO:4; amino acids 323 to 333 of ovalbumin)
Group 4: 6 mice immunized with 1 μg PBS-6-OVA
Group 5: 6 mice immunized with 1 μg PBS-14-OVA
Group 6: 6 mice immunized with 1 μg PBS-57-OVA All mice were immunized by intramuscular route at day 0 and day 14. All samples were collected 14 days following the second immunization and the IgG1 and IgG2a titers specific of ovalbumin were evaluated.

Results

Figure 4:
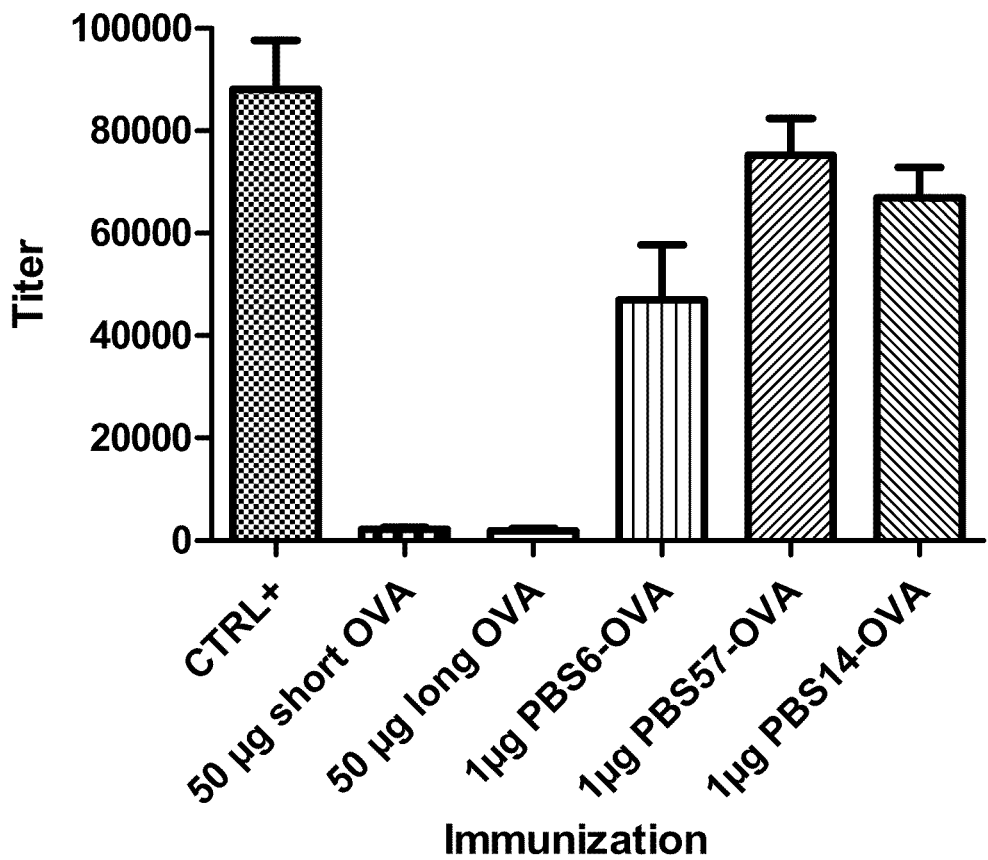
FIG. 4 shows histograms representing the titer of OVA specific IgG1 antibodies in the blood from mice immunized with ovalbumin with CFA/IFA (positive control, CTRL+), short ovalbumin peptide (50 µg short OVA), long ovalbumin peptide (50 µg long OVA), ovalbumin peptide covalently linked to PBS-6 (1 µg PBS6-OVA), ovalbumin peptide covalently linked to PBS-14 (1 µg PBS14-OVA), or ovalbumin peptide covalently linked to PBS-57 (1 µg PBS57-OVA).
Figure 5:
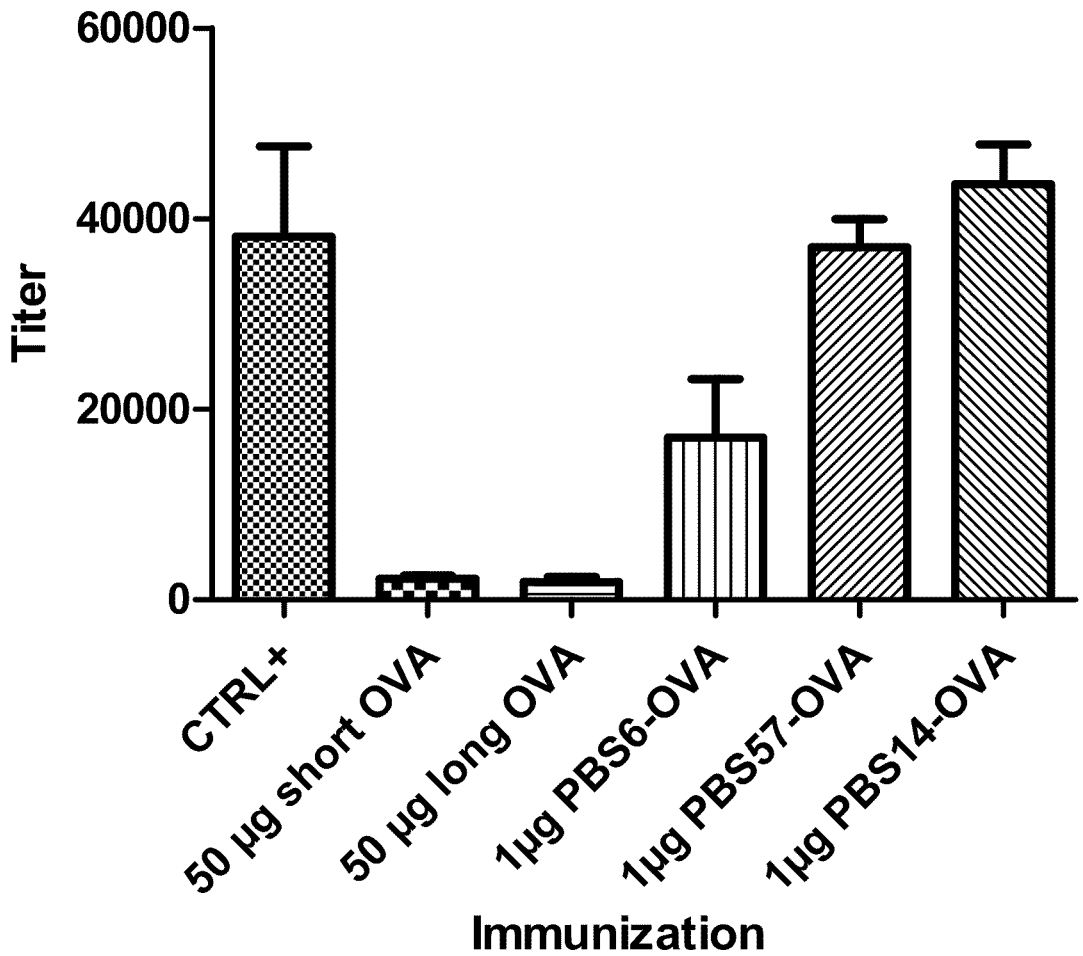
FIG. 5 shows histograms representing the titer of OVA specific IgG2a antibodies in the blood from mice immunized with ovalbumin with CFA/IFA (positive control, CTRL+), short ovalbumin peptide (50 µg short OVA), long ovalbumin peptide (50 µg long OVA), ovalbumin peptide covalently linked to PBS-6 (1 µg PBS6-OVA), ovalbumin peptide covalently linked to PBS-14 (1 µg PBS14-OVA), or ovalbumin peptide covalently linked to PBS-57 (1 µg PBS57-OVA).

Mice treated with 1 μg of OVA covalently linked to either PBS-6, PBS-14 or PBS-57, presented higher titers of both IgG1 (FIG. 4) and IgG2a (FIG. 5) specific of ovalbumin than mice treated with 50 μg of OVA alone.

Accordingly, this experiment demonstrates that the linkage between antigen and glycolipid adjuvants increase the potency of the response.

Example 5

Test Immunization Induced with Tyrosinase-Related Protein 2 (Trp2) Antigen Linked with Different Glycolipid Adjuvants Administered by Intramuscular Route Material Sixty-nine 9 week-old C57BI/6J CD45.2 female mice were used for immunisation. They were split into 14 groups: groups 1 to 5 included 3 animals, and groups 6 to 14 included 6 animals.

Target Cells for In Vivo Cytotoxicity Assay

The in vivo cytotoxicity of Trp2 181_188 induced CD8+ T cell response was evaluated by VITAL assay as described in Example 1.

Treatment of Vaccination

The Trp2 short peptide consists in the sequence of amino acids 181 to 188 of Trp2, the Trp2 long peptide consists in the sequence of amino acids 174 to 193 of Trp2 and the glycolipids used are PBS-6, PBS-14 and PBS-57.

The mice were vaccinated by intramuscular route at day 0 with the following solutions according to the different groups:
Group 1: 50 μl of PBS;
Group 2: 50 μg of Trp2 short peptide into 50 μl of PBS/DMSO;
Group 3: 50 μg of Trp2 long peptide into 50 μl of PBS/DMSO
Group 4: 1 μg of PBS-6-Trp2 into 50 μl of PBS;
Group 5: 1 μg of PBS-57-Trp2 into 50 μl of PBS;
Group 6: 1 μg of PBS-14-Trp2 into 50 μl of PBS.
Read Out:
The read out was as described in Example 1.
Results The aim of this study was to evaluate a covalent linkage of a different antigen with glycolipid NKT agonists to induce specific lysis response when it was administrated by intramuscular route, compared to the same antigen alone.

Figure 6:
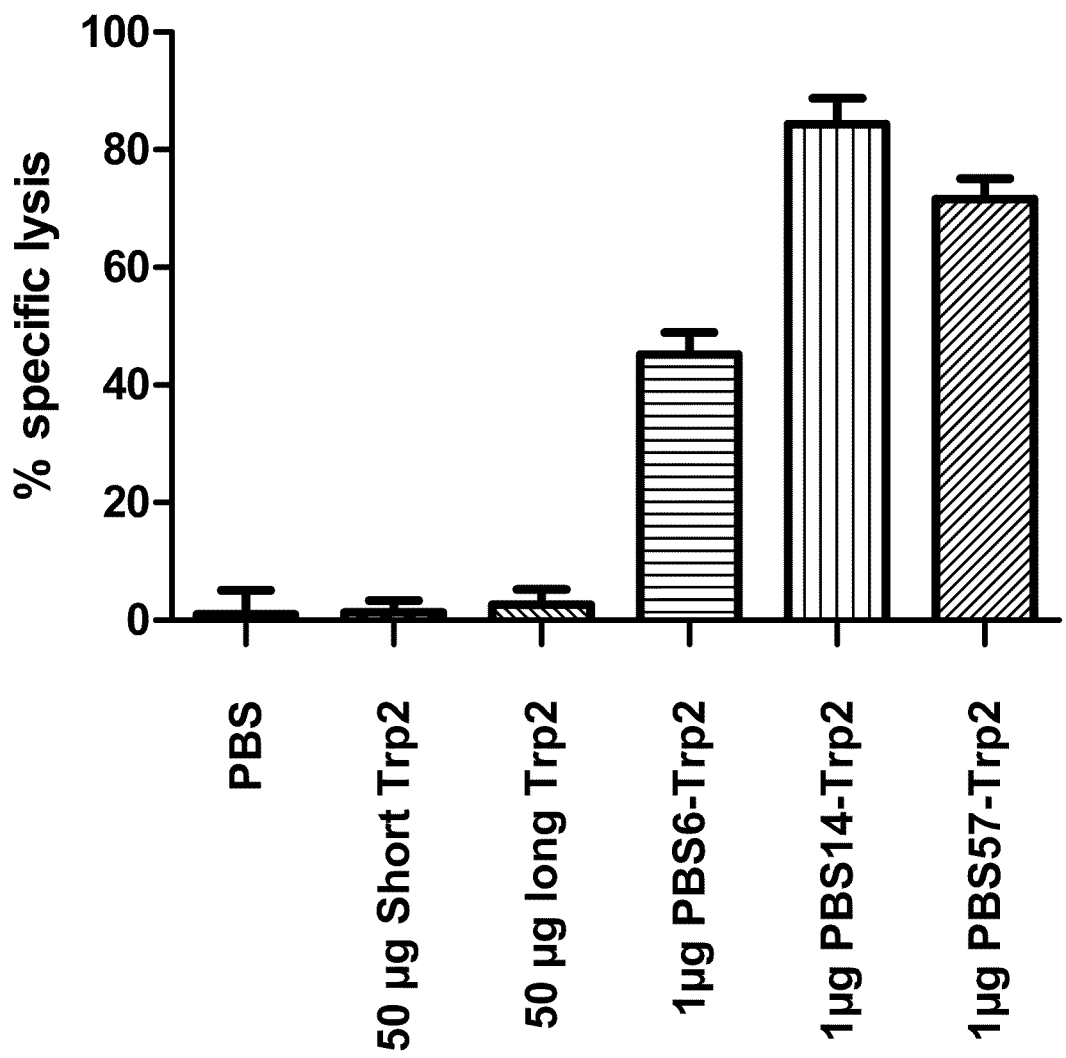
FIG. 6 shows histograms representing the percentage of Trp2 specific cytolytic activity (% specific lysis, abscissa) in the blood from mice immunized with PBS (PBS), short Trp2 peptide (50 µg short Trp2), long Trp2 peptide (50 µg long Trp2), Trp2 peptide covalently linked to PBS-6 (1 µg PBS6-Trp2), Trp2 peptide covalently linked to PBS-14 (1 µg PBS14-Trp2), or Trp2 peptide covalently linked to PBS-57 (1 µg PBS57-Trp2).

Mice treated with 1 μg of Trp2 covalently linked to either PBS-6, PBS-14 or PBS-57, presented a stronger percentage of Trp2-specific cytolytic activity in the blood than mice treated with 50 μg of Trp2 alone (FIG. 6).

Accordingly, this experiment demonstrates that the results obtained with the ovalbumin peptide covalently linked to glycolipid adjuvants are also observed with other antigens.

The invention claimed is:

1. A compound having Formula (I):

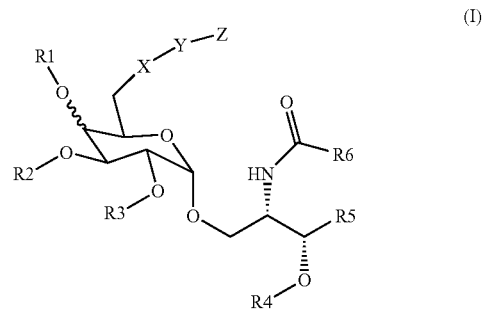

(I)

wherein,
$R_1, R_2, R_3$, and $R_4$ are each independently hydrogen, $C_1$-$C_6$ alkyl, $C_6$-$C_{12}$ aralkyl, or $C_1$-$C_6$ acyl, and $R_1$ is either above or below the sugar ring;
$R_6$ is a) —$(CH_2)_xCH_3$ where x is an integer selected from 1 to 100; or
b) —$(CH_2)_xCH=CH(CH_2)_yCH_3$ or —$(CH_2)_xCH=CH(CH_2)_yCH=CH(CH_2)_zCH_3$ wherein x, y and z are integers independently selected from 1 to 14;
$R_5$ is one of the following formulae (II), (III) or (IV)

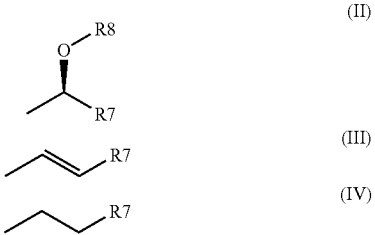

wherein $R_8$ is hydrogen, $C_1$-$C_6$ alkyl, $C_6$-$C_{12}$ aralkyl, or $C_1$-$C_6$ acyl, and
$R_7$ is a linear or branched $C_3$-$C_{100}$ alkyl;
X is —O, NH or S;
Y is a cleavable or non-cleavable linker group; and
Z is an antigen derived from an infectious agent or a tumor antigen or a pharmaceutically acceptable salt thereof.

2. The compound of claim 1, wherein $R_1, R_2, R_3, R_4$ and $R_8$ are hydrogen, $R_5$ is (II), $R_6$ is $C_{25}H_{51}$, $R_7$ is $C_{14}H_{29}$ and X is NH.

3. The compound of claim 1, wherein $R_1, R_2, R_3, R_4$ and $R_8$ are hydrogen, $R_5$ is (II), $R_6$ is $C_{23}H_{45}$, $R_7$ is $C_{14}H_{29}$ and X is NH.

4. The compound of claim 1, wherein $R_1, R_2, R_3, R_4$ and $R_8$ are hydrogen, $R_5$ is (II), $R_6$ is $C_{23}H_{47}$, $R_7$ is $C_{14}H_{29}$ and X is NH.

5. The compound according to claim 1, wherein the linker contains a protease cleavage site.

6. The compound according to claim 1, wherein the linker contains a lipase cleavage site.

7. The compound according to claim 1, wherein the linker contains a protease cleavage site and/or a lipase cleavage site.

8. The compound according to claim 1, wherein compound is capable of activating an NKT cell.

9. A vaccine composition comprising the compound of claim 1 and a physiologically acceptable vehicle.

10. A pharmaceutical composition comprising the compound of claim 1 and a physiologically acceptable vehicle.

11. A method of stimulating an immune response in a subject comprising administering to the subject an effective amount of a vaccine composition comprising a compound having Formula (I):

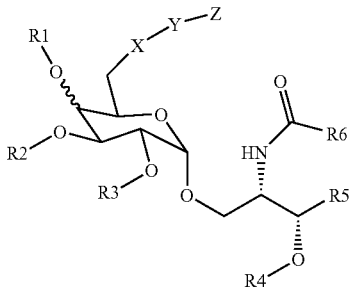

wherein, $R_1, R_2, R_3$, and $R_4$ are each independently hydrogen, $C_1$-$C_6$ alkyl, $C_6$-$C_{12}$ aralkyl, or $C_1$-$C_6$ acyl, and $R_1$ is either above or below the sugar ring;

$R_6$ is a) —$(CH_2)_x CH_3$ where x is an integer selected from 1 to 100; or b) —$(CH_2)_x CH=CH(CH_2)_y CH_3$ or —$(CH_2)_x CH=CH(CH_2)_y CH=CH(CH_2)_z CH_3$ wherein x, y and z are integers independently selected from 1 to 14;

$R_5$ is one of the following formulae (II), (III) or (IV)

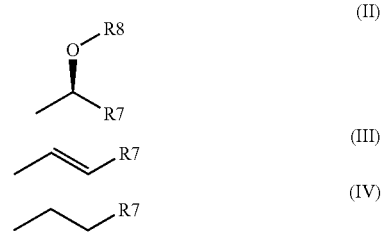

wherein $R_8$ is hydrogen, $C_1$-$C_6$ alkyl, $C_6$-$C_{12}$ aralkyl, or $C_1$-$C_6$ acyl, and $R_7$ is a linear or branched $C_3$-$C_{100}$ alkyl;

X is —O, NH or S;

Y is a cleavable or non-cleavable linker group; and

Z is an antigen derived from an infectious agent or a tumor antigen or a pharmaceutically acceptable salt thereof;

said composition further comprising a physiologically acceptable vehicle.

12. Method according to claim 11, wherein the immune response is a humoral immune response.

13. Method according to claim 11, for activating CD4+ T lymphocytes.

14. Method according to claim 11, for activating CD8+ T lymphocytes.

15. A method of treating a subject having a tumor or an infectious disease wherein said method comprises administering to the subject an effective amount of the composition of claim 10.

* * * * *